(12) United States Patent
Leinweber et al.

(10) Patent No.: US 8,349,215 B2
(45) Date of Patent: Jan. 8, 2013

(54) CORROSION INHIBITORS HAVING INCREASED BIOLOGICAL DEGRADABILITY AND MINIMIZED TOXICITY

(75) Inventors: Dirk Leinweber, Kelkheim (DE); Alexander Roesch, Oppenheim (DE); Michael Feustel, Koengernheim (DE)

(73) Assignee: Clariant Finance (BVI) Limited, Tortola (VG)

( * ) Notice: Subject to any disclaimer, the term of this patent is extended or adjusted under 35 U.S.C. 154(b) by 390 days.

(21) Appl. No.: 12/812,013

(22) PCT Filed: Dec. 10, 2008

(86) PCT No.: PCT/EP2008/010457
§ 371 (c)(1),
(2), (4) Date: Jul. 7, 2010

(87) PCT Pub. No.: WO2009/086872
PCT Pub. Date: Jul. 16, 2009

(65) Prior Publication Data
US 2010/0283010 A1    Nov. 11, 2010

(30) Foreign Application Priority Data
Jan. 10, 2008    (DE) .......................... 10 2008 003 828

(51) Int. Cl.
C23F 11/12    (2006.01)
C23F 11/14    (2006.01)
C23F 11/04    (2006.01)
C09K 15/16    (2006.01)

(52) U.S. Cl. .................. 252/389.62; 252/388; 252/390; 252/399; 252/400.62; 252/401; 507/242; 507/246; 507/939; 544/372; 548/530; 548/531; 548/546

(58) Field of Classification Search .................. 252/388, 252/389.62, 390, 399, 400.62, 401; 507/242, 507/246, 939; 544/372; 548/530, 531, 546
See application file for complete search history.

(56) References Cited

U.S. PATENT DOCUMENTS

| | | | |
|---|---|---|---|
| 2,757,125 A | 7/1956 | Mudrak | |
| 2,908,711 A | 10/1959 | Halter et al. | |
| 3,035,907 A | 5/1962 | Halter et al. | |
| 3,051,722 A | 8/1962 | Biel | |
| 3,218,264 A | 11/1965 | Katz | |
| 3,224,968 A | 12/1965 | Hinkamp | |
| 3,224,975 A | 12/1965 | Hinkamp | |
| 3,890,363 A * | 6/1975 | Malec | 558/238 |
| 4,070,370 A * | 1/1978 | Elliott et al. | 548/519 |
| 4,127,493 A | 11/1978 | Elliott et al. | |
| 5,102,882 A | 4/1992 | Kimura et al. | |
| 5,674,820 A * | 10/1997 | Manka et al. | 508/287 |
| 2009/0042747 A1* | 2/2009 | Leinweber et al. | 507/202 |
| 2009/0054268 A1 | 2/2009 | Leinweber et al. | |
| 2010/0283011 A1* | 11/2010 | Leinweber et al. | 252/392 |
| 2012/0088705 A1* | 4/2012 | Kupfer et al. | 508/297 |
| 2012/0088706 A1* | 4/2012 | Kupfer et al. | 508/297 |

FOREIGN PATENT DOCUMENTS

| | | |
|---|---|---|
| DE | 2444396 | 3/1975 |
| DE | 3701494 | 7/1987 |
| EP | 0069512 | 1/1983 |
| EP | 2031035 | 3/2009 |
| GB | 1323061 | 7/1973 |
| GB | 2040998 | 9/1980 |

OTHER PUBLICATIONS

International Search Report for PCT/EP2008/010458.
Translation of International Preliminary Examination Report for PCT/EP2008/010458.
International Search Report for PCT/EP2008/010457.
Translation of International Preliminary Examination Report for PCT/EP2008/010457.

* cited by examiner

*Primary Examiner* — Joseph D Anthony
(74) *Attorney, Agent, or Firm* — Tod A. Waldrop

(57) ABSTRACT

The invention relates to the use of salts of compound of the formula (1)

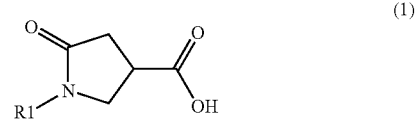

and amines of the formula (2),

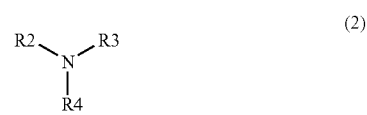

where R1 means $C_8$- to $C_{30}$-Alkyl or $C_8$- to $C_{30}$-Alkenyl, R2 means hydrogen or a group of the formula -(A-O)$_x$—H, R3, R4 mean hydrogen, $C_1$- to $C_4$-Alkyl or a group of the formula -(A-O)$_x$—H, A means $C_2$- to $C_4$-Alkylene, and x means a number from 1 to 10, as water-soluble or water-dispersible corrosion inhibitors.

6 Claims, No Drawings

CORROSION INHIBITORS HAVING INCREASED BIOLOGICAL DEGRADABILITY AND MINIMIZED TOXICITY

The present invention relates to a process for inhibiting corrosion on and in devices for extraction and transport of hydrocarbons in mineral oil extraction and processing by adding a salt of a nitrogen base and an N-substituted 5-oxopyrrolidine-3-carboxylic acid to the corrosive system.

In industrial processes in which metals come into contact with water or else with oil-water biphasic systems, there is the risk of corrosion. This is particularly marked when the aqueous phase, as in the case of mineral oil extraction and processing processes, has a high salt content or is acidic as a result of dissolved (acidic) gases such as carbon dioxide or hydrogen sulfide. The exploitation of a deposit and the processing of mineral oil are therefore impossible without specific additives to protect the equipment used.

Although suitable anticorrosives for mineral oil extraction and processing have been known for some time, they will be unacceptable in the future for offshore applications for reasons of environmental protection.

As typical prior art corrosion inhibitors, amides, amidoamines or imidazolines of fatty acids and polyamines have exceptionally good oil solubility and are therefore present only in a low concentration in the corrosive water phase owing to poor partitioning equilibria. Accordingly, these products have to be used in high dosage in spite of their poor biodegradability.

Quaternary alkylammonium compounds (quats) are alternative prior art anticorrosives which, as well as the corrosion-inhibiting properties, may also possess biostatic properties. In spite of an improved water solubility, the quats, for example compared to the imidazolines, exhibit a significantly reduced film persistence and therefore likewise lead to effective corrosion protection only in a relatively high dosage. The high algal toxicity and the moderate biodegradability are restricting the use of quats ever more to ecologically insensitive fields of use.

U.S. Pat. No. 2,757,125 describes salts of N-alkyl-4-carboxy-2-pyrrolidones, which are used as antibacterial components in cosmetic formulations or detergents. The use of these compounds as corrosion inhibitors in the oilfield chemicals sector is not described.

U.S. Pat. No. 2,908,711 and U.S. Pat. No. 3,035,907 describe oil-soluble reaction products of amines or diamines and itaconic acids, which can be used as antirust additives in fuels or mineral oils.

U.S. Pat. No. 3,218,264 discloses oil-soluble pyrrolidonecarboxylic acid-amine salts and the uses thereof as corrosion inhibitors in lubricant oils and greases. The amines used for salt formation are oil-soluble in accordance with the invention.

U.S. Pat. No. 3,224,968 likewise describes oil-soluble amine salts of pyrrolidonecarboxylic acids, which find use as antirust additives in lubricant oils. Again, oil-soluble amines (preferably $C_{12}$-$C_{20}$-alkyl-substituted) are used for amine salt formation. U.S. Pat. No. 3,224,975 describes the free pyrrolidonecarboxylic acids for the same use.

GB-A-1 323 061 discloses pyrrolidone derivatives and the use thereof in functional fluids, for example hydraulic fluids. The compounds used have $C_1$-$C_5$-alkyl substituents or $C_6$-$C_{10}$-aryl substituents on the pyrrolidone nitrogen. In hydraulic fluids, the compounds exhibit anticorrosive properties, also in combination with aliphatic amines.

EP-A-0 069 512 describes water-soluble salts of N-substituted 2-pyrrolidone-4-carboxylic acids as humectants.

It was an object of the present invention to find novel corrosion inhibitors which, combined with constant good or improved corrosion protection, and in addition to good water solubility, also give improved biodegradability and lower toxicity compared to the prior art corrosion inhibitors.

It has now been found that, surprisingly, water-soluble or water-dispersible salts of a nitrogen base and of an N-substituted 5-oxopyrrolidine-3-carboxylic acid exhibit excellent action as corrosion inhibitors, and also good biodegradeability and reduced toxicity.

The invention therefore provides for the use of salts of compounds of the formula (1)

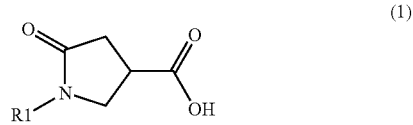

and amines of the formula (2)

in which
R1 is $C_8$- to $C_{30}$-alkyl or $C_8$- to $C_{30}$-alkenyl
R2 is hydrogen or a group of the formula -(A-O)$_x$—H
R3, R4 are each hydrogen, $C_1$- to $C_4$-alkyl or a group of the formula -(A-O)$_x$—H
A is $C_2$- to $C_4$-alkylene
x is from 1 to 10
as water-soluble or water-dispersible corrosion inhibitors.

The invention further provides a process for inhibiting corrosion at metal surfaces, especially of ferrous metals, by adding at least one salt of compounds of the formulae (1) and (2) to a corrosive system which is in contact with the metal surfaces.

Corrosive systems in the context of this invention are preferably liquid/liquid or liquid/gaseous polyphasic systems consisting of water and hydrocarbons which comprise corrosive constituents, such as salts and acids, in free and/or dissolved form. The corrosive constituents may also be gaseous, for instance hydrogen sulfide and carbon dioxide.

Hydrocarbons in the context of this invention are organic compounds which are constituents of mineral oil/natural gas, and the conversion products thereof. Hydrocarbons in the context of this invention are also volatile hydrocarbons, for example methane, ethane, propane, butane. For the purposes of this invention, they also include the further gaseous constituents of mineral oil/natural gas, for instance hydrogen sulfide and carbon dioxide.

The invention further provides for the use of the compounds of the formulae (1) and (2) as metalworking agents. In this context, the inventive compounds give very good corrosion protection even in the case of severe mechanical stress, such as in the course of grinding, cutting and drilling of metal workpieces.

In formula (1), R1 is preferably an alkyl or alkenyl group having 8 to 24 carbon atoms, especially an alkyl or alkenyl group having 8 to 18 carbon atoms. R1 is more preferably an octyl, cocoyl or oleyl radical.

R2 is preferably hydrogen or —$CH_2$—$CH_2$—OH.

R3 and R4 are each independently hydrogen, methyl, ethyl or —CH$_2$—CH$_2$—OH.

A is preferably ethylene.

x is preferably from 2 to 8. When the compound of the formula 2 contains more than one alkoxy group, x in each of these alkoxy groups may assume a different value.

The formula (2) preferably represents mono-, di- or triethanolamine. Also in accordance with the invention is the use of alkoxylated alkanolamines, for example of ethoxylated N,N-dibutylaminoethanol.

The inventive compounds can be used alone or in combination with other known corrosion inhibitors. In general, a sufficient amount of the inventive corrosion inhibitor will be used that sufficient corrosion protection is obtained under the given conditions.

Preferred use concentrations of the corrosion inhibitors based on the pure inventive salts are 5 to 5000 ppm, preferably 10 to 1000 ppm, especially 15 to 150 ppm.

The N-substituted 5-oxopyrrolidine-3-carboxylic acids are prepared as described in detail in the prior art, by reacting itaconic acid with primary amines, and can be performed as described in EP-A-0 069 512, U.S. Pat. No. 3,224,975 and U.S. Pat. No. 4,127,493.

The purity of the N-substituted 5-oxopyrrolidine-3-carboxylic acids thus obtained is generally 80-100%, in particular 88-98% and especially 90-95%.

The inventive salts of the formulae (1) and (2) are prepared by a neutralization reaction, either in substance or in a suitable solvent system, preferably mixtures of water and an alcohol. This preferably involves dissolving the amine of the formula (2) in the solvent and adding the N-substituted 5-oxopyrrolidine-3-carboxylic acid while stirring.

Amines of the formula (2) used with preference are, for example, methylamine, ethylamine, propylamine, butylamine, dimethylamine, diethylamine, dipropylamine, dibutylamine, monoethanolamine, diethanolamine, triethanolamine, N,N-dimethylamineoethanol, N,N-diethylaminoethanol, 3-dimethylaminopropanol, N,N-dipropylamieoethanol, N,N-dibutylaminoethanol, 3-aminopropanol, isopropanolamine, 2-(2-aminoethoxy) ethanol.

EXAMPLES

General Method for the Preparation of N-substituted 5-oxopyrrolidine-3-carboxylic Acid Ammonium Salts A standard stirred apparatus is initially charged with 1 mol of amine and heated to 50° C. while stirring. Then 1 mol of itaconic acid is added in portions and the reaction mixture is heated gradually to 180° C. As the reaction advances, 1 mol of water of reaction is distilled off. Subsequently, the N-substituted 5-oxopyrrolidine-3-carboxylic acid is converted to the N-substituted 5-oxopyrrolidine-3-carboxylic acid ammonium salt by adding an equimolar amount of the corresponding amine. The product obtained is characterized by acid number (AN) and basic nitrogen (bas. N). Percentages are percentages by weight based on the weight of the inventive salt.

Example 1

N-octyl-5-oxopyrrolidine-3-carboxylic acid monoethanolammonium salt 129 g of octylamine, 130 g of itaconic acid and 61 g of monoethanolamine were used to obtain 303 g of N-octyl-5-oxopyrrolidine-3-carboxylic acid monoethanolammonium salt with
AN=174 mg KOH/g and bas. N=4.6%.

Example 2

N-octyl-5-oxopyrrolidine-3-carboxylic acid triethanolammonium salt 129 g of octylamine, 130 g of itaconic acid and 149 g of triethanolamine were used to obtain 391 g of N-octyl-5-oxopyrrolidine-3-carboxylic acid triethanolammonium salt with
AN=135 mg KOH/g and bas. N=3.6%.

Example 3

N-cocoyl-5-oxopyrrolidine-3-carboxylic acid N,N-diethyl-(2-hydroxyethyl) ammonium salt 196 g of coconut amine, 130 g of itaconic acid and 117 g of N,N-diethylaminoethanol were used to obtain 428 g N-cocoyl-5-oxopyrrolidine-3-carboxylic acid N,N-diethyl(2-hydroxyethyl)ammonium salt with
AN=125 mg KOH/g and bas. N=3.3%.

Example 4

N-oleyl-5-oxopyrrolidine-3-carboxylic acid 2-(2-hydroxyethoxy)ethylammonium salt 265 g of oleylamine, 130 g of itaconic acid and 105 g of 2-(2-aminoethoxy)ethanol were used to obtain 485 g of N-oleyl-5-oxopyrrolidine-3-carboxylic acid 2-(2-hydroxyethoxy)ethylammonium salt with
AN=104 mg KOH/g and bas. N=2.8%.

Example 5

N-oleyl-5-oxopyrrolidine-3-carboxylic acid monoethanolammonium salt 265 g of oleylamine, 130 g of itaconic acid and 61 g of monoethanolamine were used to obtain 440 g of N-oleyl-5-oxopyrrolidine-3-carboxylic acid monoethanolammonium salt with
AN=113 mg KOH/g and bas. N=3.0%.

Efficacy of the Inventive Compounds as Corrosion Inhibitors

The inventive compounds were tested as corrosion inhibitors in the Shell wheel test. Carbon steel coupons (DIN 1.1203 with surface area 15 cm$^2$) were immersed into a salt-water/petroleum mixture (9:1.5% NaCl solution adjusted to pH 3.5 with acetic acid) and exposed to this medium at a peripheral speed of 40 rpm at 70° C. for 24 hours. The dosage of the inhibitor was 50 ppm of a 40% solution of the inhibitor. The protection values were calculated from the mass decrease of the coupons based on a blank value.

In the tables which follow, "comparative 1" denotes a commercial residue amine quat based on dicocoalkyldimethylammonium chloride, "comparative 2" an example from U.S. Pat. No. 3,224,975 (N-oleyl-5-oxopyrrolidine-3-carboxylic acid, prior art corrosion inhibitor), "comparative 3" an example from U.S. Pat. No. 3,224,968 (N-oleyl-5-oxopyrrolidine-3-carboxylic acid, salt with oleylamine, prior art corrosion inhibitor) and "comparative 4" an example from GB-1 323 061 (N-butyl-5-oxopyrrolidine-3-carboxylic acid, salt with dibutylamine, prior art corrosion inhibitor).

TABLE 1

(Shell wheel test)

| Example | Corrosion inhibitor | Ø % protection |
|---|---|---|
| Comparative 1 | Standard quat | 36 |
| Comparative 2 | N-oleyl-5-oxopyrrolidine-3-carboxylic acid | 60 |
| Comparative 3 | N-oley1-5-oxopyrrolidine-3-carboxylic acid, salt with oleylamine | 55 |
| Comparative 4 | N-butyl-5-oxopyrrolidine-3-carboxylic acid, salt with dibutylamine | 21 |
| 6 | Compound from example 1 | 73 |
| 7 | Compound from example 2 | 69 |
| 8 | Compound from example 3 | 90 |
| 9 | Compound from example 4 | 89 |
| 10 | Compound from example 5 | 90 |

The products were also tested in the LPR test (test conditions analogous to ASTM D 2776).

TABLE 2

(LPR test)

| | | Protection after [%] | | |
|---|---|---|---|---|
| Example | Corrosion inhibitor | 10 min | 30 min | 60 min |
| Comparative 1 | Standard quat | 54 | 61 | 74 |
| Comparative 2 | N-oley1-5-oxopyrrolidine-3-carboxylic acid | 2 | 10 | 23 |
| Comparative 3 | N-oley1-5-oxopyrrolidine-3-carboxylic acid, salt with oleylamine | 1 | 8 | 17 |
| Comparative 4 | N-butyl-5-oxopyrrolidine-3-carboxylic acid, salt with dibutylamine | 4 | 12 | 25 |
| 11 | Compound from example 1 | 65 | 79 | 86 |
| 12 | Compound from example 2 | 59 | 76 | 81 |
| 13 | Compound from example 3 | 91 | 96 | 99 |
| 14 | Compound from example 4 | 90 | 96 | 99 |
| 15 | Compound from example 5 | 91 | 95 | 99 |

As is evident from the above test results, the inventive products have very good corrosion properties at low dosage and are clearly superior to the efficacy of the prior art inhibitors.

TABLE 3

Biodegradability (OECD 306) and toxicity (EC$_{50}$ Skeletonema costatum)

| Example | Corrosion inhibitor | Biodegradability [%] | Toxicity EC$_{50}$ [mg/l] |
|---|---|---|---|
| Comparative 1 | Standard quat | 15 | <1 |
| 16 | Compound from example 1 | 85 | >100 |
| 17 | Compound from example 5 | 78 | >100 |

As is clearly evident from table 4, the inventive compounds exhibit better biodegradability and lower toxicity than the comparative example from the prior art.

The invention claimed is:

1. A process for aqueous corrosion inhibiting comprising the step of treating an article with a composition comprising at least one salt of a compound of the formula (1)

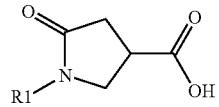

(1)

and at least one amine of the formula (2)

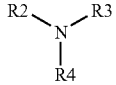

(2)

wherein
R1 is $C_8$- to $C_{30}$-alkyl or $C_8$- to $C_{30}$-alkenyl
R2 is hydrogen or a group of the formula -(A-O)$_x$—H
R3, R4 are each hydrogen, $C_1$- to $C_4$-alkyl or a group of the formula -(A-O)$_x$—H
A is $C_2$- to $C_4$alkylene
x is from 1 to 10.

2. A process as claimed in claim 1, wherein R1 is an alkyl or alkenyl group of 8 to 18 carbon atoms.

3. A process as claimed in claim 1, wherein one, two or all R2, R3 and R4 radicals are —CH$_2$—CH$_2$—OH.

4. A process as claimed in claim 1, wherein x is from 2 to 10.

5. A process as claimed in claim 1, wherein the article is a device for extraction and transport of hydrocarbons in mineral oil extraction and processing.

6. A process as claimed in claim 1, wherein the article is a device for metalworking.

* * * * *